United States Patent
Champagne et al.

(10) Patent No.: US 9,439,870 B2
(45) Date of Patent: Sep. 13, 2016

(54) ACTIVE AGENT MICROPARTICLES

(71) Applicant: COATEX, Genay (FR)

(72) Inventors: Clementine Champagne, Lyons (FR);
Jean-Marc Suau, Lucenay (FR);
Olivier Guerret, Pern (FR)

(73) Assignee: COATEX, Genay (FR)

( * ) Notice: Subject to any disclaimer, the term of this patent is extended or adjusted under 35 U.S.C. 154(b) by 0 days.

(21) Appl. No.: 14/133,716

(22) Filed: Dec. 19, 2013

(65) Prior Publication Data
US 2014/0178485 A1 Jun. 26, 2014

Related U.S. Application Data

(60) Provisional application No. 61/740,482, filed on Dec. 21, 2012.

(30) Foreign Application Priority Data

Dec. 20, 2012 (FR) ...................... 12 62499

(51) Int. Cl.
| | |
|---|---|
| *A61K 8/11* | (2006.01) |
| *C08L 33/08* | (2006.01) |
| *C08L 91/06* | (2006.01) |
| *A61K 9/50* | (2006.01) |
| *C11D 3/50* | (2006.01) |
| *C08L 33/10* | (2006.01) |
| *C08L 33/14* | (2006.01) |
| *C11D 3/18* | (2006.01) |
| *C11D 3/20* | (2006.01) |
| *C11D 3/382* | (2006.01) |
| *C11D 3/384* | (2006.01) |
| *C11D 17/00* | (2006.01) |
| *B01J 13/08* | (2006.01) |
| *C09B 67/02* | (2006.01) |
| *D06M 23/12* | (2006.01) |
| *F28D 20/02* | (2006.01) |
| *A61K 8/31* | (2006.01) |
| *A61Q 19/00* | (2006.01) |
| *A61K 8/81* | (2006.01) |
| *C09B 67/46* | (2006.01) |
| *C08K 5/01* | (2006.01) |
| *C08F 220/28* | (2006.01) |

(52) U.S. Cl.
CPC .............. *A61K 9/5031* (2013.01); *A61K 8/11* (2013.01); *A61K 8/31* (2013.01); *A61K 8/8152* (2013.01); *A61K 9/5026* (2013.01); *A61Q 19/00* (2013.01); *B01J 13/08* (2013.01); *C08K 5/01* (2013.01); *C08L 33/08* (2013.01); *C08L 33/10* (2013.01); *C08L 33/14* (2013.01); *C08L 91/06* (2013.01); *C09B 67/009* (2013.01); *C09B 67/0097* (2013.01); *C11D 3/181* (2013.01); *C11D 3/2093* (2013.01); *C11D 3/382* (2013.01); *C11D 3/384* (2013.01); *C11D 3/505* (2013.01); *C11D 17/0039* (2013.01); *D06M 23/12* (2013.01); *F28D 20/023* (2013.01); *A61K 2800/10* (2013.01); *A61K 2800/56* (2013.01); *C08F 2220/286* (2013.01)

(58) Field of Classification Search
CPC ............ C08F 2220/286; C08F 220/06; C08F 2220/1808; C08L 91/06; C08L 33/08; C08L 33/10; A61K 2800/56; A61K 8/11; A61K 8/31; A61K 8/8152; A61K 9/5026; A61K 9/5031; A61K 2800/10; A61Q 19/00; B01J 13/08; C08K 5/01; C09B 67/009; C09B 67/0097; C11D 17/0039; C11D 3/181; C11D 3/2093; C11D 3/382; C11D 3/384; C11D 3/505; D06M 23/12; F28D 20/023
See application file for complete search history.

(56) References Cited

U.S. PATENT DOCUMENTS

| | | | |
|---|---|---|---|
| 2008/0146486 A1 | 6/2008 | Boardman et al. | |
| 2010/0152094 A1 | 6/2010 | Guerret et al. | |
| 2010/0267564 A1* | 10/2010 | Moro et al. .................. | 504/320 |
| 2012/0016024 A1* | 1/2012 | Ibe et al. ..................... | 514/549 |

FOREIGN PATENT DOCUMENTS

| | | |
|---|---|---|
| FR | 2 775 441 A1 | 9/1999 |
| FR | 2 916 655 A1 | 12/2008 |
| WO | WO 2008/058833 A1 | 5/2008 |
| WO | WO 2010110167 A1 * | 9/2010 |

OTHER PUBLICATIONS

International Search Report issued Apr. 14, 2014 in PCT/FR2013/052996 (with English translation of categories of cited documents).

* cited by examiner

*Primary Examiner* — Abigail Fisher
(74) *Attorney, Agent, or Firm* — Oblon, McClelland, Maier & Neustadt, L.L.P.

(57) ABSTRACT

The present invention concerns polymeric-enveloped microparticles including at least one HASE type acrylic copolymer, at least one solid-liquid phase change material with a phase transition temperature ranging from 20 to 90° C., and at least one active agent. In particular, the microparticles include at least one HASE type acrylic copolymer including at least one anionic monomer with a polymerizable vinyl group and a carboxyl group, at least one non-ionic hydrophobic monomer with a polymerizable vinyl group, and at least one alkoxylated associative macromonomer with a polymerizable vinyl group and a hydrophobic hydrocarbon chain.

11 Claims, 6 Drawing Sheets

ACTIVE AGENT MICROPARTICLES

REFERENCE TO PRIOR APPLICATIONS

This application claims priority to U.S. provisional application Ser. No. 61/740,482, filed Dec. 21, 2012; and to French patent application 12 62499, filed Dec. 20, 2012, both incorporated herein by reference.

FIELD OF THE INVENTION

The present invention relates the area of active agent encapsulations, particularly active agent encapsulations agents using HASE type acrylic copolymers.

BACKGROUND OF THE INVENTION

Micro-encapsulation techniques are increasingly being developed and are widely used in the pharmaceutical, cosmetic, textile, agro-food, agrochemical, detergent and paint industries. Many hydrophilic or hydrophobic active agents can be encapsulated, such as odourant molecules, pharmaceutical active ingredients, cosmetic agents, photochromic or photoluminescent pigments, etc.

Encapsulation is an effective method for protecting an active agent from the external environment (pH, light, oxygen, humidity, etc.) thus preventing adverse phenomena such as light and/or oxygen-induced reactions. Encapsulation also helps protect an active agent from other molecules, and thus avoid incompatibility issues. Encapsulation also limits the degradation of an active agent during product conversion or storage processes. It can also make the handling or storage of these active agents easier.

There are many known methods of encapsulation. Thus, it has been suggested to encapsulate active agents by in-situ polymerization, by solvent extraction or again, by coacervation.

For example, it has been suggested to encapsulate active agents such as pharmaceutical active ingredients or agrochemical substances using HASE type acrylic polymers.

One of the major problems related to encapsulation remains the control of the subsequent release of the encapsulated active agent. For certain applications, it is important that the release of the active agent be triggered at the desired time in order for it to perform its functions. The release of the agent must therefore be able to intervene in response to a stimulus. For other applications, it is important to delay the release of the active agent (controlled release). For example, when the active agent is an odourant agent, especially an odourant agent that is chemically unstable or vulnerable to external stresses, it is important to ensure that it is stable in the initial formulation (lye, paint, scented formulations) but also stable after application to a surface (textile, wall, skin). An increase in remanence is therefore typically sought. The encapsulation processes proposed so far are generally inflexible in the method of triggering or controlling the release of the active agent, with the capsules formed usually releasing the active agent in response to a single stimulus. Thus, depending on the areas of application (for example, the pharmaceutical, cosmetic, textile, agro-food, agrochemical, detergent, paint industry) of the type of active agents, of the desired method of release, it is necessary to choose a suitable method of encapsulation.

Therefore, there is a need for the development of particles that can release an active agent in response to various stimuli, or that can delay its release. A need also exists for the development of a versatile method for the protection of an active agent, that is, a process that allows the protection of different types of active agents and enables their triggered release and/or their controlled release when one or the other is sought. This process will preferably be environmental friendly.

BRIEF DESCRIPTION OF THE INVENTION

The present invention relates to polymeric-enveloped microparticles as well as aqueous dispersions containing these microparticles. The polymeric-enveloped microparticles include:
  a. at least one HASE type acrylic copolymer;
  b. at least one solid-liquid phase change material with a phase transition temperature ranging from 20 to 90° C.;
  c. at least one active agent.

The present invention also concerns the use of these microparticles or the aqueous dispersions containing them to release an active agent in response to a change in pH, a change in temperature and/or to friction.

The present invention also concerns the use of these microparticles or the aqueous dispersions containing them for the preparation of cosmetic, agrochemical, paint, textile, detergent or paper products.

The present invention also concerns a process for the preparation of an aqueous dispersion of microparticles including the following steps:
  a) preparation of an aqueous solution containing:
    at least one HASE type acrylic copolymer solubilised in the said aqueous solution by means of a base,
    at least one active agent; and
    at least one solid-liquid phase change material, the said solid-liquid phase change material being present in, or having been introduced into the aqueous solution at a temperature greater than its phase transition temperature; and
  b) coacervation of the HASE type acrylic polymer to lead to the said aqueous dispersions of microparticles.

Finally, the present invention concerns a process for the preparation of solid particles from an aqueous dispersion of microparticles by drying.

DEFINITION

Figure 1:
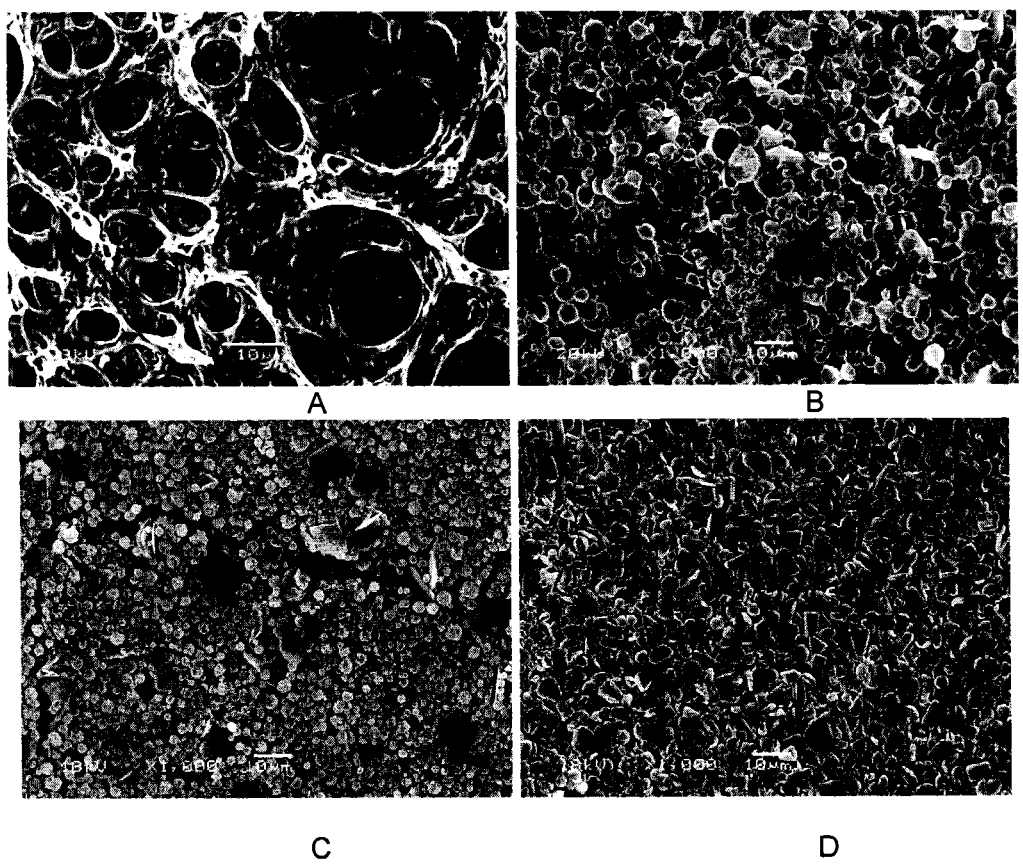
FIG. 1 represents microparticles that do not belong to the present invention (A) and microparticles of the present invention (B, C and D) observed by confocal microscopy.

In the description of the invention, the term "HASE" is an acronym for "Hydrophobically modified Alkali-soluble Emulsions".

In the description of the present invention, the expression "HASE type acrylic copolymer" means linear or cross-linked copolymers with acidic groups and hydrophobic groups. HASE type copolymers are the result of the copolymerization of anionic monomers such as (meth)acrylic acids, non-ionic hydrophobic monomers and of hydrophobic associative macromonomers. At a low pH (typically less than 5) and without the addition of a base, the HASE type acrylic copolymer is insoluble in water and is present in the form of latex. When a base is added, the anionic groups are neutralized, and the copolymer is solubilised in water.

In the description of the present invention, "solid-liquid phase change material" means a material that has the ability to change state, reversibly, in a temperature range of 20 to 90° C. The phase change material used in the composition of the microparticles of the present invention is solid at a temperature less than its phase transition temperature, and liquid at a temperature greater than its phase transition temperature. "Phase transition temperature" designates the melting temperature of the material or the temperature corresponding to the solid—liquid transition of the phase change material.

In the description of the present invention, the term "active agent" or "active ingredient" means any compound which is of interest for encapsulation.

In the description of the present invention, unless stated otherwise, the percentages expressed represent the percentages by weight, and are expressed relative to the total weight of the reference point. For example, where it is indicated that a copolymer consists of 10% of a monomer, it is understood that the copolymer includes 10% by weight of this monomer relative to the total weight of this copolymer.

In the description of the present invention, the expression "at least one" means one or more compounds (for example: one or more HASE type acrylic copolymers, one or more phase change materials, one or more active agents) such as a mixture of 2 to 5 compounds.

In the description of the present invention, the term "microparticles" means particles with an average size ranging from 0.5 μm to tens of micrometers, such as 0.5 to 100 μm, or 1 to 70 μm, or 1 to 40 μm. When the microparticles are spherical particles, the average particle size refers to the mean diameter of the particles. When the particles are not spherical, that is, when they have a longer dimension and a shorter dimension, the average particle size refers to the size of the longest dimension of the particles. The size of the particles can be measured by methods well known to the person skilled in the art, such as by laser granulometry.

"Polymeric-enveloped microparticles" or "composite microparticles" or "microcapsules", means microparticles with an outer envelope consisting of a copolymer according to the invention, and containing an active agent according to the invention.

In the description of the invention, the letters "n", "m" and "p" refer to integers.

DETAILED DESCRIPTION OF THE INVENTION

The polymeric-enveloped microparticles of the present invention effectively protect an active agent. Advantageously, the polymeric-enveloped microparticles of the present invention allow a release of the active agent in response to a change in pH, a change in temperature and/or an increase in mechanical stresses (friction). The method for the release of the active agent is selected according to the nature of the active agent and its subsequent use. The mechanical strength of the polymeric-enveloped microparticles of the present invention can be controlled. It becomes possible to limit the degradation of the microparticles over time and thus, for example, to control the passive diffusion of the active agent over time.

The polymeric-enveloped microparticles of the present invention can be in the form of an aqueous dispersion or they can be in the form of solid microparticles.

The polymeric-enveloped microparticles of the present invention include:
  at least one HASE type acrylic copolymer;
  at least one solid-liquid phase change material with a phase transition temperature ranging from 20 to 90° C., and
  at least one active agent.
HASE Type Acrylic Copolymer;
HASE type acrylic copolymers form the outer envelope of the microparticles of the present invention.

According to the methods of embodiment of the invention, the HASE type acrylic copolymers entering into the composition of the microparticles of the present invention include the following monomers:
  a) at least one anionic monomer with a polymerizable vinyl group and a carboxyl group;
  b) at least one non-ionic hydrophobic monomer with a polymerizable vinyl group; and
  c) at least one alkoxylated associative macromonomer with a polymerizable vinyl group and a hydrophobic hydrocarbon chain.

Anionic monomers with a polymerizable vinyl group and a carboxyl group are monomers with a negative charge in a basic aqueous solution. Anionic monomers with a polymerizable vinyl group and a carboxyl group are, for example, chosen from acrylic acid and/or methacrylic acid.

Non-ionic hydrophobic monomers with a polymerizable vinyl group are monomers that are neither positively nor negatively charged in aqueous solution. Non-ionic hydrophobic monomers with a polymerizable vinyl group are, for example, chosen from the esters, the amides or the nitriles of acrylic or methacrylic acid, or from acrylonitrile, vinyl acetate, styrene, methylstyrene, diisobutylene, vinylpyrrolidone or vinylcaprolactame. In particular, the non-ionic hydrophobic monomers with a polymerizable vinyl group can be chosen from the $C_1$-$C_8$ alkyl acrylates or the $C_1$-$C_8$ akyl methacrylates such as methyl acrylate, ethyl acrylate, butyl acrylate, 2-ethylhexyl acrylate, methyl methacrylate, ethyl methacrylate, butyl methacrylate or their mixtures. In particular, the non-ionic hydrophobic monomers with a polymerizable vinyl group can be chosen from ethyl acrylate, butyl acrylate, ethyl methacrylate or their mixtures.

The alkoxylated associative macromonomer with a polymerizable vinyl group and a hydrophobic hydrocarbon chain can have the following formula (I):

　　　　(I)

in which:
A represents a polymeric chain consisting of:
  m units of alkylene oxide with the formula —$CH_2CHR_1O$— with $R_1$ representing an alkyl group including 1 to 4 carbons, for example, a methyl or ethyl group, and m ranging from 0 to 150,
  p units of alkylene oxide with the formula —$CH_2CHR_2O$— with $R_2$ representing an alkyl group including 1 to 4 carbons, for example, a methyl or ethyl group, and p ranging from 0 to 150, n units of ethylene oxide with n varying from 0 to 150, or from 10 or 15 to 150, or from 10 or 15 to 100, or from 15 to 50, or from 15 to 30, in which m+n+p>4, or m+n+p≥5, and in which the units of alkylene oxide with the formula —CH$_2$CHR$_1$O—, the units of alkylene oxide with the formula —CH$_2$CHR$_2$O— and the units of ethylene oxide are in a block, alternate or are random;

R represents a radical containing a polymerizable unsaturated group belonging to the group of acrylic, methacrylic, maleic, itaconic or crotonic esters; and R' represents a linear, connected or branched hydrocarbon chain including from 6 to 40 carbon atoms, or from 7 to 35 or carbon atoms, or from 8 to 20 carbon atoms, or from 8 to 16 carbon atoms, or a substituted or non-substituted cycloalkyl or aryl group including from 6 to 100 carbon atoms, or from 6 to 60 carbon atoms.

The R$_1$ and R$_2$ groups can be identical or different.

In particular methods of embodiment, the alkoxylated associative macromonomer with a polymerizable vinyl group and a hydrophobic hydrocarbon chain has the following formula (I):

R-A-R'  (I)

in which R, R', and A are as defined above, with n representing a number of ethylene oxide units ranging from 15 to 150, or from 15 to 50, or from 15 to 30.

In particular methods of embodiment, the alkoxylated associative macromonomer with a polymerizable vinyl group and a hydrophobic hydrocarbon chain has the following formula (I):

R-A-R'  (I)

in which R represents a radical containing a polymerizable unsaturated group belonging to the group of acrylic or methacrylic esters, and A and R' are as defined in the methods of embodiment described above.

In particular methods of embodiment, the alkoxylated associative macromonomer with a polymerizable vinyl group and a hydrophobic hydrocarbon chain has the following formula (I):

R-A-R'  (I)

in which R' represents a linear, connected or branched hydrocarbon chain including from 8 to 20 carbon atoms or from 8 to 16 carbon atoms, preferably a linear hydrocarbon chain with from 8 to 18 carbon atoms, or from 8 to 14 carbon atoms, or a connected or branched chain with from 12 to 20 carbon atoms, or from 12 to 16 carbon atoms, and A and R are as defined in the methods of embodiment described above.

In particular methods of embodiment, the alkoxylated associative macromonomer with a polymerizable vinyl group and a hydrophobic hydrocarbon chain has the following formula (I):

R-A-R'  (I)

in which A, R and R' are as defined in the methods of embodiment described above, with m and p representing 0 respectively.

In particular methods of embodiment, the alkoxylated associative macromonomer with a polymerizable vinyl group and a hydrophobic hydrocarbon chain has the following formula (I):

R-A-R'  (I)

in which:
A is as defined in the methods of embodiment described above, with m and p representing 0 respectively, and n ranging from 15 to 150, or from 15 to 50, or from 15 to 30 (thus, A represents a polymeric chain consisting of 15 to 150, or from 15 to 50, or from 15 to 30 ethylene oxide units);

R represents a radical containing a polymerizable unsaturated group belonging to the group of acrylic, methacrylic, maleic, itaconic or crotonic esters, preferably belonging to the group of acrylic or methacrylic esters; and R' represents a linear, connected or branched hydrocarbon chain consisting of from 6 to 40 carbon atoms, or from 7 to 35 carbon atoms, or from 8 to 20 carbon atoms, or from 8 to 16 carbon atoms.

In particular methods of embodiment, the alkoxylated associative macromonomer with a polymerizable vinyl group and a hydrophobic hydrocarbon chain has the following formula (I):

R-A-R'  (I)

in which:
A is as defined in the methods of embodiment described above, with m and p representing 0 respectively, and n ranging from 15 to 150, or from 15 to 50, or from 15 to 30 (thus A represents a polymeric chain consisting of 15 to 150, or from 15 to 50, or from 15 to 30 ethylene oxide units);

R represents a radical containing a polymerizable unsaturated group belonging to the group of acrylic or methacrylic esters; and R' represents a linear, connected or branched hydrocarbon chain including from 8 to 20 carbon atoms, for example, a linear hydrocarbon chain containing from 8 to 18 carbon atoms, or from 8 to 14 carbon atoms, or a connected or branched alkyl chain containing from 12 to 20 carbon atoms, or from 12 to 16 carbon atoms.

In particular methods of embodiment, the acrylic copolymers used in the composition of the particles of the present invention include:

a) at least one anionic monomers with a polymerizable vinyl group and a carboxyl group chosen from acrylic acid, methacrylic acid or their mixture;

b) at least one non-ionic hydrophobic monomers with a polymerizable vinyl group chosen from ethyl acrylate, methyl methacrylate, butyl acrylate or their mixtures; and c) at least one alkoxylated associative macromonomer with a polymerizable vinyl group and a hydrocarbon chain with the following formula (I):

R-A-R'  (I)

in which A, R and R' are as defined in the methods of embodiment described above.

In particular methods of embodiment, the acrylic copolymers used in the composition of the particles of the present invention include:

a) at least one anionic monomer with a polymerizable vinyl group and a carboxyl group chosen from acrylic acid, methacrylic acid or their mixture;

b) at least one non-ionic hydrophobic monomer with a polymerizable vinyl group chosen from ethyl acrylate, methyl methacrylate, butyl acrylate or their mixtures;

c) at least one alkoxylated associative macromonomer with a polymerizable vinyl group and a hydrophobic hydrocarbon chain with formula (I):

R-A-R'  (I)

in which:
A is as defined in the methods of embodiment described above, with m and p representing 0 respectively, and n ranging from 15 to 150, or from 15 to 50, or from 15 to 30 (thus, A represents a polymeric chain consisting of 15 to 150, or from 15 to 50, or from 15 to 30 ethylene oxide units);
R represents a radical containing a polymerizable unsaturated group belonging to the group of acrylic, methacrylic, maleic, itaconic or crotonic esters, preferably belonging to the group of acrylic or methacrylic esters;
R' represents a linear, connected or branched hydrocarbon chain including from 8 to 20 carbon atoms, or from 8 to 16 carbon atoms, more particularly, a linear hydrocarbon chain containing from 8 to 18 carbon atoms, or from 8 to 14 carbon atoms, or a connected or branched hydrocarbon chain containing from 12 to 20 carbon atoms, or from 12 to 16 carbon atoms.

The acrylic copolymers used in the composition of the particles of the present invention typically include:
a) from 20% to 65%, or from 30% to 45% by weight of at least one anionic monomer with a polymerizable vinyl function and a carboxyl group;
b) from 35% to 75%, or from 45% to 60% by weight of at least one non-ionic hydrophobic monomer with a polymerizable vinyl function; and
c) from 0.5% to 15%, or from 1% to 12% by weight of at least one alkoxylated associative macromonomer with a polymerizable vinyl group and a hydrophobic hydrocarbon chain, more particularly, of an alkoxylated associative macromonomer with the following formula (I):

R-A-R'  (I)

in which A, R and R' are as defined in the methods of embodiment described above.

In particular methods of embodiment, the acrylic copolymers used in the composition of the particles of the present invention include:
a) from 20% to 65%, or from 30% to 45% by weight of at least one anionic monomer with a polymerizable vinyl group and a carboxyl group chosen from acrylic acid, methacrylic acid or their mixture;
b) from 35% to 75%, or from 45% to 60% by weight of at least one non-ionic hydrophobic monomer with a polymerizable vinyl group chosen from ethyl acrylate, methyl methacrylate, butyl acrylate or their mixtures; and
c) from 0.5% to 15%, or from 1% to 12% by weight of at least one alkoxylated associative macromonomer with a polymerizable vinyl group and a hydrophobic hydrocarbon chain with the formula (I):

R-A-R'  (I)

in which:
A is as defined in the methods of embodiment described above, with m and p representing 0 respectively, and n ranging from 15 to 150, or from 15 to 50, or from 15 to 30 (thus, A represents a polymeric chain consisting of 15 to 150, or from 15 to 50, or from 15 to 30 ethylene oxide units);
R represents a radical containing a polymerizable unsaturated group belonging to the group of acrylic, methacrylic, maleic, itaconic or crotonic esters, preferably to the group of acrylic or methacrylic esters; and
R' represents a linear, connected or branched hydrocarbon chain including from 8 to 20 carbon atoms, or from 8 to 16 carbon atoms, more particularly, a linear hydrocarbon chain containing from 8 to 18 carbon atoms, or from 8 to 14 carbon atoms, or a connected or branched hydrocarbon chain containing from 12 to 20 carbon atoms, or from 12 to 16 carbon atoms.

The HASE type acrylic copolymers involved in the composition of the particles of the present invention are the result of the copolymerization of the monomers described above. They can be prepared according to the methods described in WO 2011/104599, WO 2011/104600 and EP1778797.

During polymerization, a chain transfer agent can be added to control the molecular weight of the copolymer. The chain transfer agent can be chosen from the mercaptans such as ethyl mercaptan, n-propyl mercaptan, n-butyl mercaptan, isobutyl mercaptan, t-butyl mercaptan, n-amyl mercaptan, isoamyl mercaptan, t-amyl mercaptan, n-hexyl mercaptan, cyclohexyl mercaptan, n-octyl mercaptan, n-decyl mercaptan or n-dodecyl mercaptan.

Phase change material

The particles of the present invention include at least one solid-liquid phase change material. The phase change material has the capacity to change state, reversibly, in a temperature range from 20 to 90° C., or from 25 to 80° C., or from 35 to 70° C.

The phase change materials involved in the composition of the particles of the present invention can be chosen from the natural or synthetic waxes. Natural waxes include animal waxes, vegetable waxes and mineral waxes.

Animal and vegetable waxes generally consist of a mixture of long hydrocarbon chain lipids such as fatty acids, fatty alcohols or fatty acid or fatty alcohol esters, or even the ethers. "Long hydrocarbon chain", means hydrocarbon chains with 10 to 40 carbon atoms, for example. Animal and vegetable waxes typically have a phase transition temperature varying from 25° C. to 90° C. Examples of vegetable waxes include the waxes of carnauba, candelilla, cane sugar, esparto or shea butter. Examples of animal waxes include beeswax or lanolin.

Mineral waxes, including the paraffin waxes (commonly known as paraffin), generally consist of straight chain saturated hydrocarbons including from 20 to 40 carbon atoms, for example. Mineral waxes typically have a phase transition temperature varying from 25° C. to 90° C. Examples of mineral waxes include ceresin, ozokerite, paraffin waxes and microcrystalline waxes. Examples of paraffin waxes include heneicosane, with a melting point of 40.5° C., eicosane, with a melting point of 36.1° C. and nonadecane, with a melting point of 32.1° C.

Synthetic waxes generally consist of long hydrocarbon chains devoid of functional groups. Examples of synthetic waxes include polyethylene-based polymers and polyalkylene glycol-based polymers such as polyethylene glycol-based and polypropylene glycol-based polymers.

The phase change materials involved in the composition of the microparticles of the present invention can be chosen from the long chain hydrocarbon alcohols, for example, the alcohols with from 14 to 30 carbon atoms, or from 14 to 22 carbon atoms, such as myristyl alcohol, cetyl alcohol, stearic alcohol, arachidic alcohol, behenic alcohol, the long hydrocarbon chain fatty acids, for example, the acids with from 12 to 30 carbon atoms, or from 12 to 22 carbon atoms, such as decanoic acid, lauric acid, myristic acid, palmitic acid, stearic acid, arachidic acid, behenic acid, the fatty acid esters such as the esters of decanoic acid, lauric, myristic acid, palmitic acid, stearic acid, arachidic acid, behenic acid, the fatty ethers, or their mixtures.

The phase change materials used in the composition of the particles of the present invention will be selected with regard to the subsequent use of the particles.

Active Agent

The microparticles of the present invention include at least one active agent.

The active agent can be chosen from the fragrances or odorous molecules (for example, menthol, honeysuckle, cananga oil, citronellal, aurantiol or limonene), the essential oils, aromas, opacifiers, moisturizing agents, softening agents, freshening agents, dyes, plasticisers, thinning agents, pharmaceutical active ingredients, inks, pigments such as photochromic or photoluminescent pigments, agrochemical active ingredients, antiseptics, detergents, enzymes, anti-foaming, bleaching agents, optical brighteners or antibacterial agents. Terpene, terpineol and citronelol can also be used.

In certain methods of embodiment of the present invention, the active agent is a fragrance or an odourant molecule.

The Microparticles of the Present Invention

In certain methods of embodiment, the microparticles of the present invention include, relative to the total weight of the microparticles:
- from 1 to 20%, or from 1 to 15%, or from 1 to 10% by weight of at least one HASE type acrylic copolymer as described above;
- from 4 to 95%, or from 4 to 75%, or from 4 to 50% by weight of at least one phase change material as described above; and
- from 4 to 95%, or from 24 to 95%, or from 49 to 95% by weight of at least one active agent as described above.

The microparticles of the present invention may be in the form of an aqueous dispersion of particles, or they may be in the solid form, that is to say, in the form of solid granules (or microcapsules). Thus, the present invention concerns aqueous dispersions including microparticles as described above, and solid microparticles with a composition as described above.

The aqueous dispersions of microparticles may include 1 to 70% by weight of microparticles.

The microparticles of the present invention release the encapsulated active agent in response to a change in pH, a change in temperature and/or to friction. It is possible in the context of the present invention to adjust the mechanical strength of the microparticles so as to control the release of the active agent.

"Control the release of the active agent" means both to trigger the release of the active agent in response to a stimulus, or to delay this release over time. Thus, it is possible to trigger the release of the active agent at the desired time depending on the desired application or the effect sought. Also, it is possible to make one or more microparticles of the present invention sensitive to one or more stimuli, and thus enable the release of the encapsulated active agent at the desired time.

Advantageously, the microparticles of the present invention offer good mechanical strength, or even a mechanical strength greater than that of the particles that do not include phase change materials. Such characteristics are particularly advantageous when the encapsulated active agent is a fragrance or an odourant molecule. Indeed, when the active agent is a fragrance or an odourant molecule, it is typically sought to increase its remanence. The microparticles of the present invention thus allow a controlled release of the encapsulated active agent, their degradation thus being delayed.

The microparticles of the present invention thus offer a minimum mechanical strength such that they maintain their integrity after having been sheared for 2 min at 200 $s^{-1}$ at 25° C. according to the method described in the "examples" section. Thus, according to this aspect, the microparticles of the present invention are said to have "controlled mechanical strength".

The concentrations of HASE type acrylic copolymer, of phase change material and/or of active agent can be adjusted in order to obtain microparticles that are more or less resistant to mechanical pressures; in other words, with a mechanical strength that is greater than or equal to the minimum mechanical strength as described above. In fact, for certain applications, it is desirable to obtain microparticles that release the active agent under weak mechanical stresses (low mechanical pressures) while for other applications, it is desirable to obtain particles that are resistant to mechanical stresses that are more or less strong.

The microparticles of the present invention can be used to release an active agent in response to a change in pH, to a change in temperature and/or to friction.

The dispersions or microparticles of the present invention can be used in the cosmetics field, for example to formulate lotions, shampoos, creams, deodorants, makeup compositions, care compositions. In this regard, in particular can be cited the encapsulation of fragrances, essential oils, opacifiers, moisturizing agents, softening agents, freshening agents, thinning agents.

Figure 6:
FIG. 6 represents microscopy images of a cotton fabric dipped into a solution containing 1.5% test B particles and then dried at room temperature.

The dispersions or microparticles of the present invention can be used in the textile industry, for example in the manufacture of clothing, pantyhose, stockings, gloves. In particular in this regard, the encapsulation of fragrances, thinning agents, anti-perspirants and antibacterial agents can be cited. The dispersions or microparticles are thus applied to various textiles (FIG. 6).

The dispersions or microparticles of the present invention can be used in the paint field, where dyes, pigments or resins can in particular be encapsulated.

The microparticles of the present invention can be used in the paper industry (encapsulation of inks, of odourant molecules) or detergent manufacturing fields (encapsulation of odourant agents, anti-foaming agents, whiteners).

Thus, the solid microparticles or aqueous dispersions of microparticles of the present invention can be used for the preparation of cosmetic products, agrochemicals, detergents, paints, textiles, paper.

Preparation of Aqueous Dispersions of Particles, and Particles of the Present Invention An object of the present invention also concerns a process for the preparation of an aqueous dispersion of microparticles, as well as a process for the preparation of polymeric-enveloped microparticles as described above. The solid microparticles of the present invention are generally produced from an aqueous dispersion of microparticles.

The aqueous dispersions of microparticles can be prepared by a process involving the following steps:
  a) preparation of an aqueous solution containing:
    at least one HASE type acrylic copolymer solubilised in the said aqueous solution by means of a base, specifically a HASE type acrylic copolymer as described above;
    at least one active agent, specifically at least one active agent as described above; and
    at least one solid-liquid phase change material, specifically, at least one solid-liquid phase change material as described above, the said solid-liquid phase change material being present in, or having been introduced into the aqueous solution at a temperature greater than its phase transition temperature; and b) coacervation of the HASE type acrylic polymer to lead to the said aqueous dispersions of microparticles.

When the solid-liquid phase change material is said to be "present in the aqueous solution at a temperature greater than its phase transition temperature", it is understood that the aqueous solution including the HASE type acrylic copolymer, the base, the active agent and the phase change material is at a temperature greater than the phase transition temperature of the phase change material.

When the solid-liquid phase change material is said to "have been introduced into the aqueous solution at a temperature greater than its phase transition temperature", it is understood that the material was added at a temperature greater than its phase transition temperature, but that the water, the base and the HASE type copolymer, the active agent can be at a temperature lower than this phase transition temperature. The final aqueous solution consisting of the HASE type acrylic copolymer, the base, the active agent and the phase change material generally has a temperature that is lower than the phase transition temperature of the phase change material.

In general, the solid-liquid phase change material, alone or in a mixture with the active agent, is heated to a temperature greater than its phase transition temperature and is introduced at a temperature greater than its phase transition temperature into an aqueous solution including the HASE type acrylic copolymer, the base and possibly the active agent, this aqueous solution generally having a temperature less than the phase transition temperature of the phase change material.

In step a), the base is added in a quantity sufficient to make the HASE type acrylic copolymer soluble in the aqueous solution.

The base used in the process is typically an organic or mineral base. For example, the base can be selected from sodium hydroxide, ammonia, lime, potassium carbonate and 2-amino-2-methyl-1-propanol.

The articles of Jenkins et al., 2002 (J. Phys. Chem. B 2002, 106, 1195-1204 1195) and Horiuchi et al., 1998 (Can. J. Chem. 76: 1779-1787) describe the phenomenon of HASE polymer solubilisation when a base is added.

According to the methods of embodiment of the invention, the quantity of base used to solubilise the copolymer is such that the pH of the aqueous solution is greater than or equal to 6.5, or greater than or equal to 7, or greater than or equal to 7.5.

According to other methods of embodiment of the invention, on the basis of the type of base used, particularly if the base used is sodium hydroxide, the quantity of base used to solubilise the copolymer is such that the molar ratio ($nOH^-$/nCOOH) between the number of hydroxyl groups provided by the base ($nOH^-$) and the number of carboxyl groups provided by the HASE type acrylic copolymer (nCOOH) is greater than 0.3, or greater than 0.4, or greater than 0.45 and preferably less than 1.2. The number of carboxyl groups provided by the HASE type acrylic copolymer can be determined by methods known to the person skilled in the art, such as by titration.

According to methods of embodiments of the invention, the aqueous solution of step a) is prepared under agitation.

The coacervation step of the HASE type acrylic polymer leading to the aqueous dispersions of microparticles (step b)) is carried out once the aqueous solution is at a temperature lower than the phase transition temperature of the phase change material, i.e., after cooling of the aqueous solution.

Coacervation can be achieved by the addition of salts such as sodium chloride, or alternatively, by the addition of an acid.

In certain methods of embodiment of step b) of the process, coacervation is achieved by adding an acid. The acid used in the process may in particular be selected from an organic or mineral acid. In particular, the acid can be chosen from phosphoric acid, hydrochloric acid, acetic acid, citric acid, D-gluconic acid, glutamic acid and ascorbic acid.

In certain methods of embodiment of step b) of the process, the amount of acid used to carry out the coacervation is such that the pH of the dispersion is less than or equal to 6.5 or less than or equal to 6.3.

In other methods of embodiment of step b) of the process, depending on the type of acid used, especially if the acid used is acetic acid, the amount of acid added is such that the molar ratio ($nH_3O^+$/nCOOH) between the number of protons supplied by the acid ($nH_3O^+$) and the number of carboxyl groups supplied by the HASE type acrylic copolymer (nCOOH) is greater than 0.1, or greater than 0.15, or greater than 0.2 and lower than 1.

According to methods of embodiment of the invention, the addition of salt or acid is carried out under agitation.

The coacervation (or precipitation) of the HASE type acrylic polymer results in the formation of a polymeric envelope which constitutes the outer envelope of the microparticles.

In certain methods of embodiment, the aqueous solution including the solubilised HASE type acrylic copolymer, the active agent and the solid-liquid phase change material (step a)) is prepared according to the following steps:

a1) preparation of an aqueous solution containing the HASE type acrylic copolymer solubilised by means of a base;

a2) preparation of a mixture including the active agent and the phase change material, the said mixture being prepared at a temperature greater than the phase transition temperature of the phase change material, or then being heated to a temperature greater than the phase transition temperature of the phase change material; and a3) introduction of the mixture obtained in step a2) into the aqueous solution obtained in step a1).

It is noted that according to these methods of embodiment, during step a3):

the mixture obtained in step a2) is at a temperature greater than the phase transition temperature of the phase change material, for example, at a temperature between the phase transition temperature of the phase change material and the heating temperature of the mixture a2);

the aqueous solution obtained in step a1) is at a temperature lower than the phase transition temperature of the phase change material.

According to the methods of embodiment of the invention, the introduction of the mixture obtained in step a2) into the aqueous solution obtained in step a1) is performed under agitation.

In other methods of embodiment, the aqueous solution including the solubilised HASE type acrylic copolymer, the active agent and the solid-liquid phase change material (step a)) can be prepared according to the following steps:

a1) preparation of an aqueous solution containing the HASE type acrylic copolymer solubilised by means of a base, at least one active agent and at least one phase change material; and a2) heating of the aqueous solution obtained in step a1) to a temperature greater than the transition temperature of the phase change material.

According to the methods of embodiments of the invention, the aqueous solution is prepared (step a1)) under agitation, or it is agitated after having been prepared. In this case, it can be agitated before, during or after heating, (step a2)), but before performing step b).

According to these methods of embodiment, the order of introduction of the HASE type acrylic copolymer, the base, the active agent and the phase change material to lead to the aqueous solution of step a1) is indifferent.

Thus, the HASE type acrylic copolymer, the water and the base can be mixed together as a first step. To this mixture can be added a second mixture consisting of the phase change material and the active agent in order to obtain the aqueous solution of step a1). Alternatively, the HASE type acrylic copolymer, the water, the base, the phase change material and the active agent can be mixed together, without a preliminary sub-mixing step, to yield the aqueous solution of step a1).

Thus, according to the present invention, the aqueous dispersions of particles can be prepared by a process involving the following steps:
- a1) preparation of an aqueous solution including a base and at least one HASE type acrylic copolymer, specifically, a HASE type acrylic copolymer as described above;
- a2) preparation of a mixture including at least one active agent and at least one phase change material, the said mixture being prepared at a temperature greater than the phase transition temperature of the phase change material;
- a3) introduction of the mixture obtained in step a2) into the aqueous solution obtained in step a1); and
- b) coacervation of the HASE type acrylic copolymer to lead to the aqueous dispersions of particles.

Alternatively, the aqueous dispersions of particles of the present invention can be prepared by a process involving the following steps:
- a1) preparation of an aqueous solution including a base, at least one active agent, at least one phase change material and at least one HASE type acrylic copolymer, specifically, a HASE type acrylic copolymer as described above;
- a2) heating of the aqueous solution obtained in step a1) to a temperature greater than the transition temperature of the phase change material; and
- b) coacervation of the HASE type acrylic copolymer to lead to the aqueous dispersions of particles.

Solid microparticles can be obtained after drying of the microparticle dispersions obtained in step b).

The HASE type acrylic copolymer, the phase change material and the active agent used in the processes of the present invention can be as described in the description of the present invention.

The processes implemented for the preparation of the microparticles of the present invention are environmentally friendly, because they do not make use of organic solvents.

Process for the Formulation of an Active Agent

In one aspect, the present invention relates to a process for the formulation of an active agent including the preparation of microparticles including at least one HASE type acrylic copolymer, at least one phase change material and at least one active agent, the said formulation allowing a controlled release of the active agent.

EXAMPLES

Preparation of HASE 1 Acrylic Copolymer

The acrylic copolymer according to the invention is prepared using methods known to the person skilled in the art by means of a mercaptan chain transfer agent.

This copolymer consists of:
35.5% by weight of methacrylic acid,
52.4% by weight of ethyl acrylate,
12.0% by weight of a macromonomer with formula (I) in which:
  m and p=0,
  n=30,
  R represents a methacrylic ester,
  R' represents a connected hydrocarbon chain including 12 carbon atoms.

Preparation of a Microparticle Dispersion According to the Present Invention (ref.1)

Preparation of an Aqueous Solution 7.5 g of HASE 1 copolymer (polymerized to 30.8% in water) are solubilised in 61.9 g of water in the presence of 2.9 g of 10% sodium hydroxide by agitation in a mixer at a temperature of 40° C. In this case, it is noted that $nOH^-=7.25\times10^{-3}$ and $nCOOH=9.5\times10^{-3}$. The pH of the solution is around 8.5.

15.75 g of paraffin marketed by the Sigma-Aldrich Corporation under the reference Paraffin wax 327204 ($T_f$=53-57° C.) are mixed with 47.25 g of limonene. The mixture is agitated and heated to a temperature of about 80° C.

Using a peristaltic pump, the liquid paraffin-limonene mixture (at a temperature between the Tf and 80° C.) is introduced into the HASE 1 copolymer aqueous solution.

Coacervation 6.44 g of a 4% solution of $H_3PO_4$ are added to the aqueous solution of the HASE 1 copolymer to which was added the paraffin-limonene mixture. The pH is measured.

The particles obtained are characterized by laser granulometry using the Malvern Mastersizer 2000 ($D_{50\%}$: diameter corresponding to 50% of the particle volume cumulative frequency). The results are presented in table 1.

Preparation of a Microparticle Dispersion According to the Present Invention (ref.2)

Preparation of an Aqueous Solution 15.75 g of paraffin marketed by the Sigma-Aldrich Corporation under the reference Paraffin wax 327204 ($T_f$=53-57° C.) are mixed with 47.25 g of limonene and the mixture is heated to 80° C.

In parallel, 7.5 g of HASE 1 copolymer (polymerized to 30.8% in water) are solubilised in 61.9 g of water in the presence of 2.9 g of 10% sodium hydroxide by agitation in a mixer at a temperature of 40° C. In this case, it is noted that $nOH^-=7.25\times10^{-3}$ and $nCOOH=9.5\times10^{-3}$. The pH of the solution is around 8.5.

The aqueous solution of the HASE 1 copolymer and paraffin-limonene mixture are mixed and heated to 80° C.

The whole is mixed using a mixer and the temperature is allowed to gradually decrease.

Coacervation

When the mixture reaches 40° C., 6.44 g of a 4% solution of $H_3PO_4$ is added. The pH is measured.

The particles obtained are characterized by laser granulometry using the Malvern Mastersizer 2000 ($D_{50\%}$: diameter corresponding to 50% of the particle volume cumulative frequency). The results are presented in table 1.

TABLE 1 particle granulometry

| Ref. | HASE 1 mass content (%) | Wax mass content (%) | AP mass content (%) | final pH | $D_{50\%}$ (μm) |
|---|---|---|---|---|---|
| 1 | 3.5 | 24.1 | 72.3 | 6.2 | 2.76 |
| 2 | 3.5 | 24.1 | 72.3 | 6.7 | 3.66 |

Study of the Variation in Wax Content, in Active Agent, in HASE 1 Copolymer, and Study of the Variation in the Nature of the Wax, the Nature of the Active Agent The particle dispersions presented below (table 2) were prepared according to the method used to prepare ref. 1.

The particles obtained are characterized by laser granulometry using the Malvern Mastersizer 2000 ($D_{50\%}$: diameter corresponding to 50% of the particle volume cumulative frequency). The results are presented in table 2.

TABLE 2

Particle granulometry

| Test | Wax | Active agent | HASE 1 mass content (%) | Wax mass content (%) | Active agent mass content (%) | final pH | $D_{50\%}$ (μm) |
|---|---|---|---|---|---|---|---|
| A | — | Limonene | 3.5 | 0 | 96.5 | 6.3 | 1.94 |
| B | Paraffin 1 | Limonene | 3.5 | 24.1 | 72.3 | 6.3 | 2.80 |
| C | Paraffin 1 | Limonene | 3.5 | 24.1 | 72.3 | 6.2 | 2.76 |
| D | Paraffin 1 | Limonene | 3.5 | 24.1 | 72.3 | 6.3 | 2.99 |
| E | Paraffin 1 | Limonene | 4.3 | 23.9 | 71.8 | 6.2 | 1.85 |
| F | Paraffin 1 | Limonene | 5.3 | 23.7 | 71.0 | 6.1 | 1.56 |
| G | Paraffin 1 | Citronellal | 3.5 | 24.1 | 72.3 | 6.3 | 1.82 |
| H | Paraffin 2 | Limonene | 3.5 | 24.1 | 72.3 | 6.2 | 2.79 |
| I | Nacol ether 18 (Sasol) | Limonene | 3.5 | 24.1 | 72.3 | 6.3 | 3.20 |
| J | Paraffin 1 | Geranyl acetate | 3.5 | 24.1 | 72.3 | 6.1 | 2.88 |
| K | Paraffin 1 | Limonene | 2.7 | 24.3 | 73.0 | 6.3 | 6.09 |
| L | Paraffin 1 | Limonene | 3.5 | 14.5 | 82.0 | 6.7 | 2.84 |
| M | Paraffin 1 | Limonene | 2.2 | 24.4 | 73.3 | 6.5 | 5.84 |
| N | Paraffin 1 | Limonene | 3.5 | 33.8 | 62.7 | 6.4 | 3.20 |

Paraffin 1: Paraffin wax 327204 from Sigma-Aldrich $T_f$ = 53-57° C.
Paraffin 2: Paraffin wax 411663 from Sigma-Aldrich $T_f$ > 65° C.

Test A represents the prior art (absence of a phase change material). The other tests are according to the invention.

It is observed that the presence of a phase change material (or wax) improves the mechanical strength of the capsules (FIG. 1). FIG. 1A (above, left: test A) shows that the particles deprived of wax did not resist drying and the vacuum metalizing of the samples (no particles or particle residues visible). These particles do not display the minimum mechanical strength necessary to maintain their integrity.

Figure 2:
FIG. 2 represents microparticles of the present invention observed by confocal microscopy.

On the other hand, the particles according to the present invention (FIGS. 1A, 1B and 1C, test B, test I and test H respectively) have maintained their integrity after drying and vacuum metalizing (which are very destructive conditions). FIG. 2 shows the microparticles of the present invention obtained according to test B.

Study of the Resistance of Particles to Shearing

Particle shear strength is evaluated using the $D_{50\%}$ (Mastersizer 2000 Malvern) of dispersions with a 47±1% particle content sheared in a Couette double cell of the HAAKE Mars III rheometer (shearing for 120 s at 25° C.). The $D_{50\%}/D^0_{50\%}$ variation is represented as a function of the applied shear gradient ($D^0_{50\%}$ corresponds to the $D_{50\%}$ of the dispersion of non-sheared particles). When $D_{50\%}/D^0_{50\%}$ decreases, it means that the integrity of the particles is not maintained. The particles, which are in fact the residue of particles, are then measured by laser granulometry.

Figure 3:
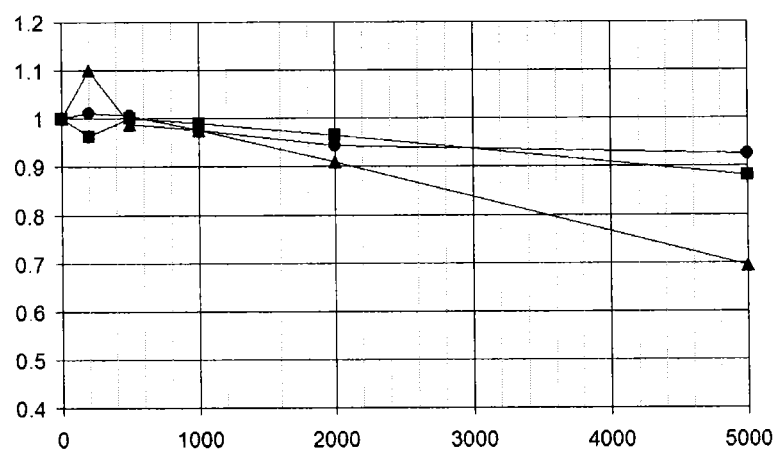
FIG. 3 represents the $D_{50\%}/D^0{}_{50\%}$ variation in microparticles (ordinate) as a function of the shear gradient applied (DG/dt in 1/s) (x-axis) for different mass contents of HASE type acrylic copolymer.

FIG. 3 enables an evaluation of the influence of the HASE 1 polymer content on the shear strength of the microparticles ($D_{50\%}/D^0_{50\%}$ as a function of the shear gradient applied for different tests, circles=test C, squares=test M, triangles=test K). It is shown that the lower the HASE content, the lower the shear strength of the particles.

Figure 4:
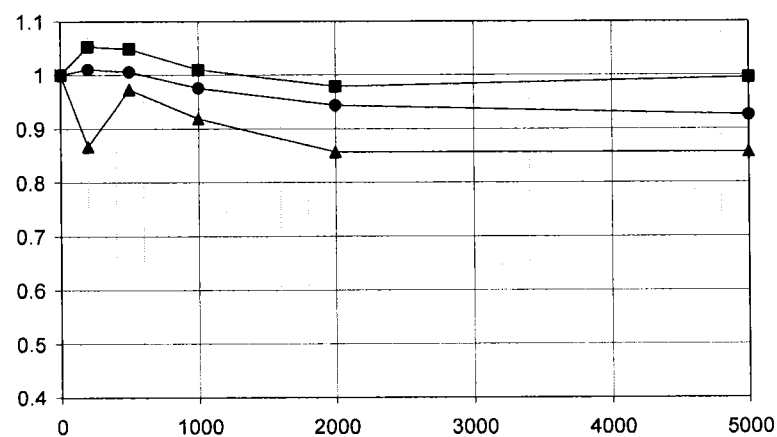
FIG. 4 represents the $D_{50\%}/D^0{}_{50\%}$ variation in microparticles (ordinate) as a function of the shear gradient applied (DG/dt in 1/s) (x-axis) for variable paraffin/limonene ratios.

FIG. 4 enables an evaluation of the influence of the wax content on the shear strength of the microparticles ($D_{50\%}/D^0_{50\%}$ as a function of the shear gradient applied for different tests, squares=test L, circles=test C, triangles=test N). It is shown that the higher the wax content, the less the shear strength of the particles.

Figure 5:
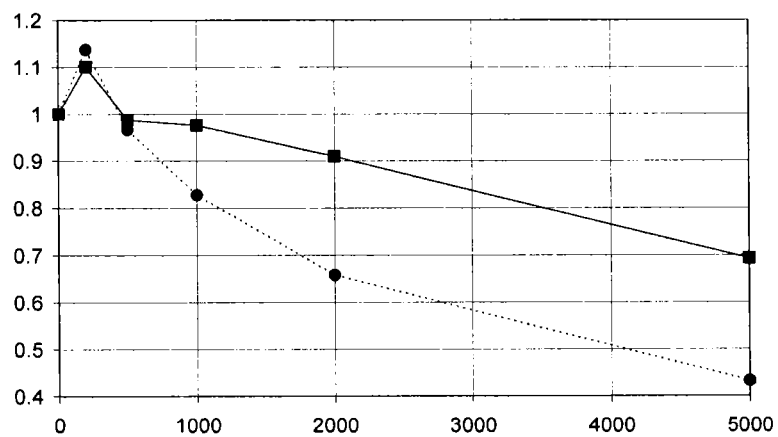
FIG. 5 represents the $D_{50\%}/D^0{}_{50\%}$ variation in microparticles (ordinate) as a function of the shear gradient applied (DG/dt in 1/s) (x-axis) for variable pHs.

FIG. 5 enables an evaluation of the influence of the final pH of the dispersions on the shear strength of the microparticles ($D_{50\%}/D^0_{50\%}$ as a function of the shear gradient applied for test K, squares=the dispersion at a pH of 6.1, circles: pH=the dispersion at a pH of 11.7)

The invention claimed is:

1. Polymeric-enveloped microparticles, comprising:
   a) 1 to 20% by weight of an acrylic copolymer of HASE type, the acrylic polymer comprising in polymerized form:
      an anionic monomer with a polymerizable vinyl function and a carboxyl group;
      a non-ionic hydrophobic monomer with a polymerizable vinyl function; and
      an alkoxylated associative macromonomer with a polymerizable vinyl group and a hydrophobic hydrocarbon chain;
   b) 4 to 95% by weight of a solid-liquid phase change material with a phase transition temperature ranging from 20 to 90° C., the solid-liquid phase change material being at least one of a natural wax and a synthetic wax; and
   c) 4 to 95% by weight of an active agent which is a fragrance or odorous molecule or an agrochemical active ingredient;
   wherein the microparticles have controlled mechanical strength and provide controlled release of the active agent.

2. The polymeric-enveloped microparticies according to claim 1, wherein the HASE type acrylic copolymer comprises in polymerized form, relative to a total weight of the copolymer:
   from 20% to 65% by weight of the anionic monomer with a polymerizable vinyl function and a carboxyl group;
   from 35% to 75% by weight of the non-ionic hydrophobic monomer with a polymerizable vinyl function; and
   from 0.5% to 15% by weight of the alkoxylated associative monomer with a polymerizable vinyl group and a hydrophobic hydrocarbon chain.

3. The polymeric-enveloped microparticles according to claim 1, wherein the alkoxylated associative macromonomer of the HASE type acrylic copolymer is a macromonomer of formula (I):

$$R\text{-}A\text{-}R' \qquad (I)$$

in which:
A represents a polymeric chain consisting of:
m units of an alkylene oxide with the formula —$CH_2CHR_1O$— with $R_1$ representing an alkyl group including 1 to 4 carbons, and m ranging from 0 to 150,
p units of alkylene oxide with the formula —$CH_2CHR_2O$— with $R_2$ representing an alkyl group including 1 to 4 carbons, and p ranging from 0 to 150, and
n units of ethylene oxide, with n ranging from 0 to 150,
in which:
m+n+p >4, and
the units of alkylene oxide with the formula —$CH_2CHR_1O$—, the units of alkylene oxide with the formula —$CH_2CHR_2O$—, and the units of ethylene oxide are in a block, are alternate, or are random;
R represents a radical containing a polymerizable unsaturated group selected from the group consisting of an acrylic ester, a methacrylic ester, a maleic ester, an itaconic ester, and a crotonic ester: and
R' represents a linear or branched hydrocarbon chain having 6 to 40 carbon atoms, or a substituted or non-substituted cycloalkyl or aryl group including from 6 to 100 carbon atoms.

4. The polymeric-enveloped microparticles according to claim 3, wherein n ranges from 15 to 150.

5. The polymeric-enveloped microparticles according to claim 3, wherein R' represents a linear or branched hydrocarbon chain having from 8 to 20 carbon atoms.

6. The polymeric-enveloped microparticles according to claim 3, wherein:
m and p are each 0,
n varies from 15 to 150,
R represents a radical containing a polymerizable unsaturated group selected from the group consisting of an acrylic ester and a methacrylic ester; and
R' represents a linear hydrocarbon chain having from 8 to 18 carbon atoms, or a branched alkyl chain having from 12 to 20 carbon atoms.

7. Polymeric-enveloped microparticles according to claim 1, comprising, relative to a total weight of the microparticles:
a. 1 to 10% by weight of the HASP type acrylic copolymer;
b. 4 to 75% by weight of the phase change material; and
c. 24 to 95% by weight of the active agent, the active agent comprising at least one fragrance or odorous molecule.

8. An aqueous dispersion, comprising water and the microparticles according to claim 1.

9. A cosmetic, agrochemical, paint, textile, detergent or paper product comprising the microparticles of claim 1.

10. Polymeric-enveloped microparticles according to claim 1, wherein the active agent is a fragrance or odorous molecule.

11. Polymeric-enveloped microparticles according to claim 1, wherein the active agent is an agrochemical active ingredient.

* * * * *